United States Patent
Yamamoto

(10) Patent No.: US 10,792,014 B2
(45) Date of Patent: Oct. 6, 2020

(54) ULTRASOUND INSPECTION APPARATUS, SIGNAL PROCESSING METHOD FOR ULTRASOUND INSPECTION APPARATUS, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 701 days.

(21) Appl. No.: 14/670,108

(22) Filed: Mar. 26, 2015

(65) Prior Publication Data

US 2015/0201909 A1 Jul. 23, 2015

Related U.S. Application Data

(63) Continuation of application No. PCT/JP2013/075913, filed on Sep. 25, 2013.

(30) Foreign Application Priority Data

Sep. 27, 2012 (JP) ................... 2012-214132
Sep. 28, 2012 (JP) ................... 2012-216181

(51) Int. Cl.
*A61B 8/08* (2006.01)
*A61B 8/00* (2006.01)
(Continued)

(52) U.S. Cl.
CPC .......... *A61B 8/5223* (2013.01); *A61B 5/7221* (2013.01); *A61B 5/7246* (2013.01);
(Continued)

(58) Field of Classification Search
CPC ... A61B 8/5261; A61B 8/4245; A61B 8/0825; A61B 8/4416; A61B 8/485; A61B 8/58;
(Continued)

(56) References Cited

U.S. PATENT DOCUMENTS

2008/0242999 A1* 10/2008 Kakee ............... A61B 8/00 600/458
2010/0076312 A1* 3/2010 Katsuyama .......... A61B 8/00 600/443

(Continued)

FOREIGN PATENT DOCUMENTS

JP 2009-090102 A * 4/2009 ............ A61B 8/00
JP 2010-082190 A * 4/2010 ............ A61B 8/00

(Continued)

OTHER PUBLICATIONS

International Search Report issued in PCT/JP2013/075913 dated Oct. 22, 2013 (English Translation).

*Primary Examiner* — Keith M Raymond
*Assistant Examiner* — Patrick M Mehl
(74) *Attorney, Agent, or Firm* — Birch, Stewart, Kolasch & Birch, LLP

(57) ABSTRACT

An ultrasound inspection apparatus includes a region setting section setting a plurality of regions within the inspection object; a sound velocity calculator calculating a sound velocity of each of the plurality of regions; a sound velocity obtainer obtaining a preliminary sound velocity of a region of interest; and an image quality determiner determining an image quality of the region of interest based on the preliminary sound velocity. The preliminary sound velocity obtained by the sound velocity obtainer is employed as a sound velocity of the region of interest when a determination result made by the image quality determiner is positive, and the sound velocity of the region of interest is calculated by the sound velocity calculator when the determination result is negative.

19 Claims, 9 Drawing Sheets

(51) Int. Cl.
   *G01S 7/52* (2006.01)
   *A61B 5/00* (2006.01)
   *G01S 15/89* (2006.01)

(52) U.S. Cl.
   CPC ............ *A61B 8/4461* (2013.01); *A61B 8/469* (2013.01); *A61B 8/5246* (2013.01); *A61B 8/5269* (2013.01); *A61B 8/585* (2013.01); *G01S 7/52038* (2013.01); *G01S 7/52049* (2013.01); *G01S 15/8906* (2013.01); *A61B 2560/0475* (2013.01)

(58) Field of Classification Search
   CPC ................... G01S 15/8915; G01S 7/52049; G10K 11/346
   See application file for complete search history.

(56) References Cited

U.S. PATENT DOCUMENTS

| | | |
|---|---|---|
| 2011/0077519 A1 | 3/2011 | Katsuyama |
| 2011/0077521 A1* | 3/2011 | Katsuyama ........ G01N 29/0654 600/443 |
| 2011/0142319 A1* | 6/2011 | Lee .................... G01S 7/52063 382/131 |
| 2012/0004551 A1 | 1/2012 | Katsuyama |
| 2012/0011935 A1* | 1/2012 | Kim .................. G01S 7/52049 73/597 |
| 2012/0136250 A1* | 5/2012 | Tabaru ................... A61B 8/08 600/438 |
| 2012/0203109 A1 | 8/2012 | Tanabe et al. |
| 2012/0245467 A1* | 9/2012 | Miyachi ............. G01S 7/52074 600/447 |

FOREIGN PATENT DOCUMENTS

| | | |
|---|---|---|
| JP | 2010-119481 A | 6/2010 |
| JP | 2011-072566 A | 4/2011 |
| JP | 2011-092686 A | 5/2011 |
| JP | 2012-010943 A | 1/2012 |
| JP | 2012-157387 A | 8/2012 |
| JP | 2012-161569 A | 8/2012 |

* cited by examiner

FIG. 9

|   | 1 | 2 | 3 | 4 | 5 |
|---|---|---|---|---|---|
| 5 | OK | NG | NG | OK | OK |
| 4 | OK | NG | NG | OK | OK |
| 3 | OK | NG | NG | OK | OK |
| 2 | OK | OK | OK | OK | OK |
| 1 | OK | OK | OK | OK | OK |

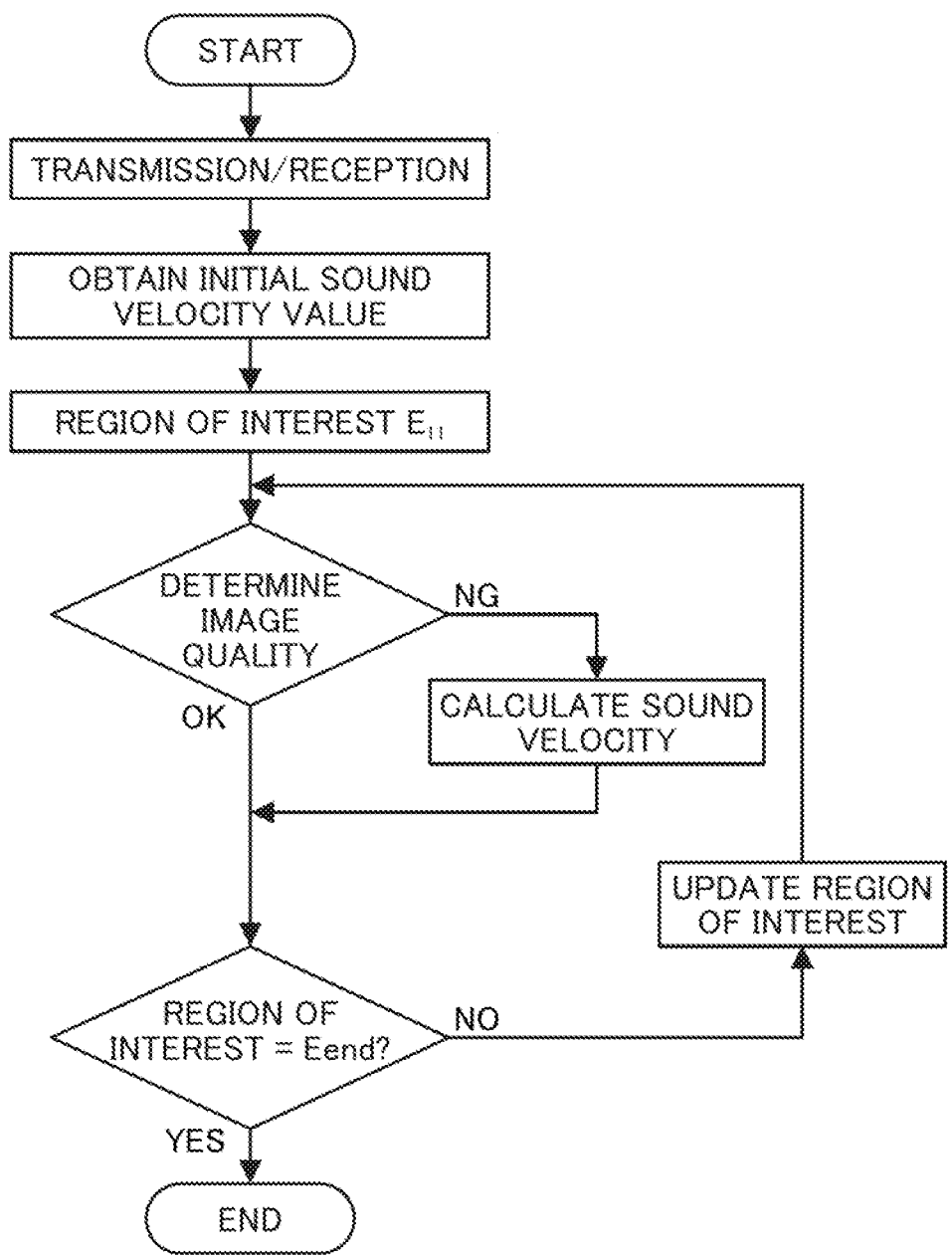

ULTRASOUND INSPECTION APPARATUS, SIGNAL PROCESSING METHOD FOR ULTRASOUND INSPECTION APPARATUS, AND RECORDING MEDIUM

CROSS-REFERENCE TO RELATED APPLICATIONS

This application is a Continuation of PCT International Application No. PCT/JP2013/075913 filed on Sep. 25, 2013, which claims priority under 35 U.S.C. § 119(a) to Japanese Application No. 2012-214132 filed on Sep. 27, 2012 and Japanese Application No. 2012-216181 filed on Sep. 28, 2012. Each of the above application(s) is hereby expressly incorporated by reference, in its entirety, into the present application.

BACKGROUND OF THE INVENTION

The invention relates to an ultrasound inspection apparatus for capturing an image of an inspection object, such as an organ in a living body, by transmitting/receiving an ultrasonic beam to generate an ultrasound image used to inspect and diagnose the inspection object, as well as to a signal processing method for the ultrasound inspection apparatus, and a recording medium having stored therein a program for the ultrasound inspection apparatus.

Conventionally, ultrasound inspection apparatuses such as ultrasound image diagnostic apparatuses using ultrasound images are put to practical use in the medical field. Generally, this type of ultrasound inspection apparatus includes an ultrasound probe provided with a plurality of elements (ultrasound transducers) and an apparatus main body connected to the ultrasound probe. Ultrasonic beams are transmitted from the plurality of elements in the ultrasound probe toward an inspection object (a subject), ultrasonic echoes from the subject are received by the ultrasound probe, and an ultrasound image is generated by electrically processing the received ultrasonic echo signals in the apparatus main body.

When an ultrasound inspection apparatus generates an ultrasound image, the plurality of elements in the probe focuses and transmits ultrasonic beams onto an inspection target region of a subject, for example, an organ in a living body, a lesion on the organ, or the like, and ultrasonic echoes are received via the plurality of elements from a surface or border of a reflecting body in the inspection target region, such as the organ, lesion, or the like. However, ultrasonic echoes reflected by the same reflecting body are received by the plurality of elements, and thus, with respect to an ultrasonic echo signal received by a transmitting element after being reflected by a reflecting body located at a focal position of the ultrasonic beam transmitted by that transmitting element, an ultrasonic echo signal reflected by the same reflecting body but received by a different element will be delayed. As such, after element data is obtained by A/D (analog/digital) converting of the ultrasonic echo signals received by the plurality of elements, a sound ray signal is generated by performing a reception focusing process on the element data, or in other words, aligning the phase of the element data by correcting the delay and performing phasing-addition. The ultrasound image is then generated based on the sound ray signal thus obtained.

In the meantime, when generating an ultrasound image, the ultrasound inspection apparatus generates the ultrasound image assuming that the sound velocity in a living body having the subject is constant. However, a sound velocity value in an actual living body changes depending on the properties of tissue in the living body, and there is a resulting variation in the sound velocity value. This variation has caused degradation in the quality of ultrasound images, such as spatial distortion, and a drop in contrast or spatial resolution.

To deal with it, in order to more accurately diagnose a diagnosis region in a subject, image qualities are recently being improved by optimizing the sound velocity values at desired diagnosis regions and reducing such image distortion, drops in spatial resolution, and the like.

For example, JP 2011-92686 A discloses an ultrasound diagnostic apparatus including a region of interest setting unit for setting a region of interest, a transmission focus instruction unit for causing an ultrasound probe to focus the transmission of ultrasonic waves onto the region of interest, a set sound velocity designating unit for designating a plurality of set sound velocities for reception focusing on an ultrasonic detection signal from the region of interest, a focus index calculating unit for performing reception focusing for each of the plurality of set sound velocities and calculating a focus index for the ultrasonic detection signal, and an ambient sound velocity determining unit for determining an ambient sound velocity of the region of interest based on the focus index for each of the plurality of set sound velocities.

JP 2011-92686 A discloses constructing a highly-accurate ultrasound image by correctly determining the ambient sound velocity for each of pixels or line images that constitute the ultrasound image, based on the focus index.

However, according to the technique disclosed in JP 2011-92686 A, although an image having a higher quality than conventional techniques can be obtained, there is a problem in that it takes time to find the ambient sound velocities for all of the pixels (lines) because the focus index is obtained in an exhaustive manner based on a plurality of set sound velocities for each of pixels or line images and the set sound velocity at which the focus index is best is taken as the optimal sound velocity (ambient sound velocity). Consequently, there is a further problem in that this causes a drop in the frame rate.

While solving the problems with the aforementioned conventional techniques, an object of the invention is to provide an ultrasound inspection apparatus capable of finding an optimal sound velocity value for each of regions in an image in a short amount of time and constructing a highly-accurate ultrasound image without causing a drop in a frame rate, and to provide a signal processing method for the ultrasound inspection apparatus, and a recording medium having stored therein a program for the ultrasound inspection apparatus.

SUMMARY OF THE INVENTION

In order to attain the objects above, the present invention provides an ultrasound inspection apparatus for inspecting an inspection object using an ultrasonic beam, the apparatus comprising a region setting section configured to set a plurality of regions within the inspection object; a sound velocity calculator configured to calculate a sound velocity of each of the plurality of regions; a sound velocity obtainer configured to take one of the plurality of regions as a region of interest and obtain a preliminary sound velocity of the region of interest; and an image quality determiner configured to determine an image quality of the region of interest based on the preliminary sound velocity obtained by the sound velocity obtainer, wherein the sound velocity obtainer obtains the preliminary sound velocity based on a sound velocity of at least one of the plurality of regions within a predetermined range from the region of interest, and wherein the preliminary sound velocity obtained by the sound velocity obtainer is employed as a sound velocity of the region of interest when a determination result made by the image quality determiner is positive, and the sound velocity of the region of interest is calculated by the sound velocity calculator when the determination result is negative.

Preferably, the sound velocity obtainer obtains the preliminary sound velocity based on the sound velocity of at least one of the plurality of regions temporally and/or spatially within a predetermined range from the region of interest.

Preferably, the one of the plurality of regions spatially within the predetermined range is a region near the region of interest in a same image.

Preferably, the one of the plurality of regions spatially within the predetermined range is a region in a same partial image when an image is regionally divided into a plurality of partial images.

Preferably, the one of the plurality of regions temporally within the predetermined range is a region corresponding to the region of interest in an image of a frame a predetermined number of frames before.

Preferably, the one of the plurality of regions temporally within the predetermined range is a region corresponding to the region of interest in at least one of images obtained by performing a predetermined process on images of a plurality of frames up to a predetermined number of frames before or a region corresponding to the region of interest in at least one of the images of the plurality of frames up to the predetermined number of frames before, the sound velocity of at least one of the plurality of regions being a sound velocity obtained by performing a predetermined process on sound velocities of the plurality of frames up to the predetermined number of frames before.

Preferably, the predetermined process on sound velocities is a process for obtaining one of an average value and a median value of the sound velocities of the plurality of frames up to the predetermined number of frames before.

In order to attain the objects above, the present invention provides an ultrasound inspection apparatus for inspecting an inspection object using an ultrasonic beam, the apparatus comprising a region setting section configured to set a plurality of regions within the inspection object; a sound velocity calculator configured to calculate a sound velocity of each of the plurality of regions; a sound velocity obtainer configured to take one of the plurality of regions as a region of interest and obtain a preliminary sound velocity of the region of interest; an initial sound velocity storage configured to store a pre-set initial sound velocity; and an image quality determiner configured to determine an image quality of the region of interest based on the preliminary sound velocity obtained by the sound velocity obtainer, wherein the sound velocity obtainer obtains the initial sound velocity stored in the initial sound velocity storage as the preliminary sound velocity, and wherein for each of the plurality of regions, the preliminary sound velocity obtained by the sound velocity obtainer is employed as a sound velocity of a region in question when a determination result made by the image quality determiner is positive, and the sound velocity of the region in question is calculated by the sound velocity calculator when the determination result is negative.

Preferably, the initial sound velocity storage stores a plurality of the initial sound velocities, and the initial sound velocity used in an image quality determination performed by the image quality determiner is selected based on an input from an operating section.

Preferably, the initial sound velocity stored in the initial sound velocity storage is a value near a sound velocity in a living body.

Preferably, the value near the sound velocity in the living body is a value from 1400 to 1700 m/s.

Preferably, the value near the sound velocity in the living body is a value from 1450 to 1550 m/s.

Preferably, the initial sound velocity stored in the initial sound velocity storage is set again based on a determination result made by the image quality determiner.

Preferably, the image quality determiner determines the image quality based on one of a sharpness, a brightness, a contrast, and a frequency of an image of the region of interest generated based on the preliminary sound velocity.

Preferably, the image quality determiner determines the image quality by comparing the image of the region of interest generated based on the preliminary sound velocity with an image of a same region in a previous image.

Preferably, the image quality determiner determines the image quality by evaluating a similarity between reference data generated based on post-phasing addition reception data of the region of interest generated based on the preliminary sound velocity, and pre-phasing addition reception data.

It is preferred to include an element data storage configured to store element data which each of elements in a transducer array outputs upon receiving an ultrasonic echo.

In order to attain the objects above, the present invention provides a signal processing method for an ultrasound inspection apparatus for inspecting an inspection object using an ultrasonic beam, the method comprising: a region setting step of setting a plurality of regions within the inspection object; a sound velocity calculating step of calculating a sound velocity of each of the plurality of regions; a sound velocity obtaining step of taking one of the plurality of regions as a region of interest and obtaining a preliminary sound velocity of the region of interest; and an image quality determining step of determining an image quality of the region of interest based on the preliminary sound velocity obtained in the sound velocity obtaining step, wherein the sound velocity obtaining step obtains the preliminary sound velocity based on a sound velocity of at least one of the plurality of regions within a predetermined range from the region of interest, and wherein the preliminary sound velocity obtained in the sound velocity obtaining step is employed as a sound velocity of the region of interest when a determination result made in the image quality determining step is positive, and the sound velocity of the region of interest is calculated in the sound velocity calculating step when the determination result is negative In order to attain the objects above, the present invention provides a computer readable recording medium having stored therein a program that causes a computer to execute signal processing for an ultrasound inspection apparatus for inspecting an inspection object using an ultrasonic beam, the program comprising: a region setting step of setting a plurality of regions within the inspection object; a sound velocity calculating step of calculating a sound velocity of each of the plurality of regions; a sound velocity obtaining step of taking one of the plurality of regions as a region of interest and obtaining a preliminary sound velocity of the region of interest; and an image quality determining step of determining an image quality of the region of interest based on the preliminary sound velocity obtained in the sound velocity obtaining step, wherein the sound velocity obtaining step obtains the preliminary sound velocity based on a sound velocity of at least one of the plurality of regions within a predetermined range from the region of interest, and wherein the preliminary sound velocity obtained in the sound velocity obtaining step is employed as a sound velocity of the region of interest when a determination result made in the image quality determining step is positive, and the sound velocity of the region of interest is calculated in the sound velocity calculating step when the determination result is negative.

In order to attain the objects above, the present invention provides a signal processing method for an ultrasound inspection apparatus for inspecting an inspection object using an ultrasonic beam, the method comprising: a region setting step of setting a plurality of regions within the inspection object; a sound velocity calculating step of calculating a sound velocity of each of the plurality of regions; a sound velocity obtaining step of taking one of the plurality of regions as a region of interest and obtaining a preliminary sound velocity of the region of interest; and an image quality determining step of determining an image quality of the region of interest based on the preliminary sound velocity obtained in the sound velocity obtaining step, wherein the sound velocity obtaining step obtains a pre-set initial sound velocity as the preliminary sound velocity, and wherein for each of the plurality of regions, the preliminary sound velocity obtained in the sound velocity obtaining step is employed as a sound velocity of a region in question when a determination result made in the image quality determining step is positive, and the sound velocity of the region in question is calculated in the sound velocity calculating step when the determination result is negative.

In order to attain the objects above, the present invention provides a computer readable recording medium having stored therein a program that causes a computer to execute signal processing for an ultrasound inspection apparatus for inspecting an inspection object using an ultrasonic beam, the program comprising: a region setting step of setting a plurality of regions within the inspection object; a sound velocity calculating step of calculating a sound velocity of each of the plurality of regions; a sound velocity obtaining step of taking one of the plurality of regions as a region of interest and obtaining a preliminary sound velocity of the region of interest; and an image quality determining step of determining an image quality of the region of interest based on the preliminary sound velocity obtained in the sound velocity obtaining step, wherein the sound velocity obtaining step obtains a pre-set initial sound velocity as the preliminary sound velocity, and wherein for each of the plurality of regions, the preliminary sound velocity obtained in the sound velocity obtaining step is employed as a sound velocity of a region in question when a determination result made in the image quality determining step is positive, and the sound velocity of the region in question is calculated in the sound velocity calculating step when the determination result is negative.

According to the invention, an optimal sound velocity value for each of regions can be found in a short amount of time, and thus a highly-accurate ultrasound image can be constructed without causing a drop in a frame rate.

BRIEF DESCRIPTION OF THE DRAWINGS

FIG. 9 is a schematic diagram illustrating region-by-region results determined by an image quality determiner.

FIG. 10 is a flowchart illustrating the operation of the ultrasound inspection apparatus illustrated in FIG. 7.

DETAILED DESCRIPTION OF THE INVENTION

An ultrasound inspection apparatus, and a signal processing method for the ultrasound inspection apparatus, and a computer readable recording medium having stored therein a program for the ultrasound inspection apparatus according to the invention will be described in detail hereinafter based on preferred embodiments illustrated in the appended drawings.

Figure 1:
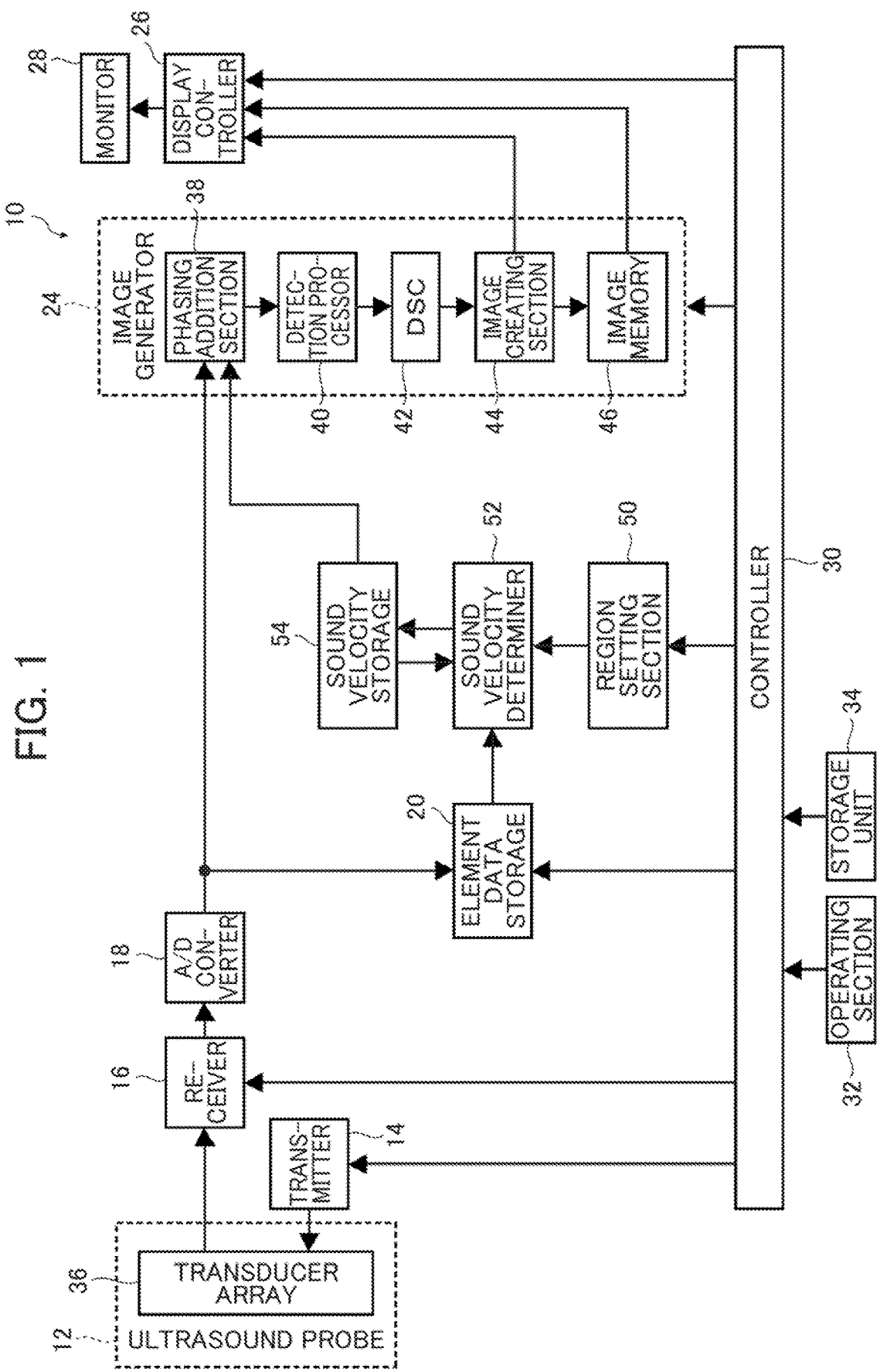
FIG. 1 is a block diagram conceptually illustrating an example of the configuration of a first embodiment of an ultrasound inspection apparatus according to the invention.

FIG. 1 is a block diagram conceptually illustrating an example of the configuration of a first embodiment of the ultrasound inspection apparatus according to the invention.

As illustrated in FIG. 1, an ultrasound inspection apparatus 10 includes an ultrasound probe 12, a transmitter 14 and receiver 16 connected to the ultrasound probe 12, an analog-to-digital (A/D) converter 18, an element data storage 20, an image generator 24, a display controller 26, a monitor 28, a controller 30, an operating section 32, a storage unit 34, a region setting section 50, a sound velocity determiner 52, and a sound velocity storage 54.

The ultrasound probe 12 has a transducer array 36 as used in a standard ultrasound inspection apparatus.

The transducer array 36 has a plurality of elements, namely ultrasound transducers, arranged in a one- or two-dimensional array. When capturing an ultrasound image of an inspection object (hereinafter, referred to as a subject), the ultrasound transducers transmit ultrasonic beams toward a subject in accordance with the respective driving signals supplied from the transmitter 14, receive ultrasonic echoes from the subject, and output reception signals (analog element signals). In this embodiment, of the plurality of ultrasound transducers in the transducer array 36, each of a predetermined number of the ultrasound transducers that makes up a group generates a corresponding component of a single ultrasonic beam. The predetermined number of ultrasound transducers in a group then generates a single ultrasonic beam to be transmitted to the subject.

Each of the ultrasound transducers comprises an element composed of a piezoelectric body and electrodes each provided on either end of the piezoelectric body, or in other words, a transducer. The piezoelectric body is composed of, for example, a piezoelectric ceramic represented by PZT (lead zirconate titanate), a piezoelectric polymer represented by PVDF (polyvinylidene fluoride), a piezoelectric monocrystal represented by PMN-PT (lead magnesium niobate-lead titanate solid solution), or the like.

When a pulse-form or continuous-waveform voltage is applied to the electrodes of the transducer, the piezoelectric body extends and constricts. As a result, pulse-form or continuous-waveform ultrasonic waves are generated from the respective transducers, and the ultrasonic beam is formed from a combination of those ultrasonic waves. Meanwhile, the respective transducers extend and constrict upon receiving the propagating ultrasonic waves and generate electrical signals, and the electrical signals are outputted as reception signals of the ultrasonic waves (analog element signals).

The transmitter 14 has, for example, a plurality of pulsers, and in accordance with a transmission delay pattern selected in response to a control signal from the controller 30, causes the ultrasonic beam components transmitted from the predetermined number of ultrasound transducers (hereinafter, referred to as ultrasound elements) that make up a group in the transducer array 36 to form a single ultrasonic beam by adjusting delay amounts of respective driving signals and supplying the driving signals to the plurality of ultrasound elements that form the group.

In response to a control signal from the controller 30, the receiver 16 amplifies and outputs a reception signal, or an analog element signal for each ultrasound element, which the transducer array 36 has outputted after receiving an ultrasonic echo produced by mutual effects between the ultrasonic beam transmitted from the transducer array 36 and the subject.

Here, in correspondence with the transmission of a single ultrasonic beam, the receiver 16 outputs a plurality of analog element signals received by the plurality of ultrasound elements as a single piece of analog element data that includes information on the receiving ultrasound elements and information on a reception time. In other words, the element data is data expressing a strength of the reception signal with respect to the position of the element and the reception time.

The receiver 16 also receives an ultrasonic echo and outputs analog element data each time an ultrasonic beam is transmitted by the transmitter 14. Accordingly, the transmitter 14 transmits an ultrasonic beam a plurality of times, and then the receiver 16 outputs a plurality of pieces of analog element data corresponding to the respective transmissions.

The receiver 16 supplies the analog element data to the A/D converter 18.

The A/D converter 18 is connected to the receiver 16, and converts the analog element data supplied from the receiver 16 into digital element data (first element data). The A/D converter 18 supplies the A/D-converted digital element data to the element data storage 20 and the image generator 24.

The element data storage 20 sequentially stores the digital element data outputted from the A/D converter 18. The element data storage 20 also stores information regarding a frame rate inputted from the controller 30 (the depth of a position at which the ultrasonic wave is reflected, the density of scanning lines, and a parameter representing the range of visual field, for example) in association with the aforementioned digital element data (hereinafter, simply referred to as element data).

Under the control of the controller 30, the image generator 24 generates a sound ray signal (reception data) from the element data supplied from the A/D converter 18 or the element data storage 20, and generates an ultrasound image from the sound ray signal.

The image generator 24 has a phasing addition section 38, a detection processor 40, a digital scan converter (DSC) 42, an image creating section 44, and an image memory 46.

In accordance with a reception direction set by the controller 30, the phasing addition section 38 selects one reception delay pattern from among a plurality of reception delay patterns stored in advance based on a sound velocity distribution stored in the sound velocity storage 54, and based on the selected reception delay pattern, carries out a reception focusing process by delaying and adding the signals of the respective elements in the element data. This reception focusing process yields reception data (sound ray signal) having an ultrasonic echo well-focused.

The phasing addition section 38 supplies the reception data to the detection processor 40.

The detection processor 40 performs, on the reception data generated by the phasing addition section 38, correction for attenuation, which is caused due to distance, based on the depth of the position at which the ultrasonic wave is reflected, and then performs an envelope detection process to generate B-mode image data that is tomographic image information related to tissues in the subject.

The DSC 42 converts the B-mode image data generated by the detection processor 40 into image data compatible with a standard television signal scanning mode (raster conversion).

The image creating section 44 creates the B-mode image data for use in inspection and display by performing various types of necessary image processing, including gradation processing and the like, on the B-mode image data inputted from the DSC 42, and then outputs the created B-mode image data for inspection or display to the display controller 26 for display or stores the B-mode image data in the image memory 46.

The image memory 46 temporarily stores the B-mode image data for inspection created by the image creating section 44. The B-mode image data for inspection stored in the image memory 46 is read out to the display controller 26 for displaying in the monitor 28 as necessary.

The display controller 26 causes the monitor 28 to display an ultrasound image based on the B-mode image signal for inspection, which has undergone image processing performed by the image creating section 44.

The monitor 28 includes a display device such as a liquid crystal display (LCD), and displays an ultrasound image under the control of the display controller 26.

The region setting section 50 sets a plurality of regions in an image capturing region that is to undergo scanning by ultrasonic waves, in response to an input made by an operator through the operating section 32 or in response to an instruction from the controller 30. In this apparatus, an appropriate sound velocity is determined on this region-by-region basis.

Figure 3:
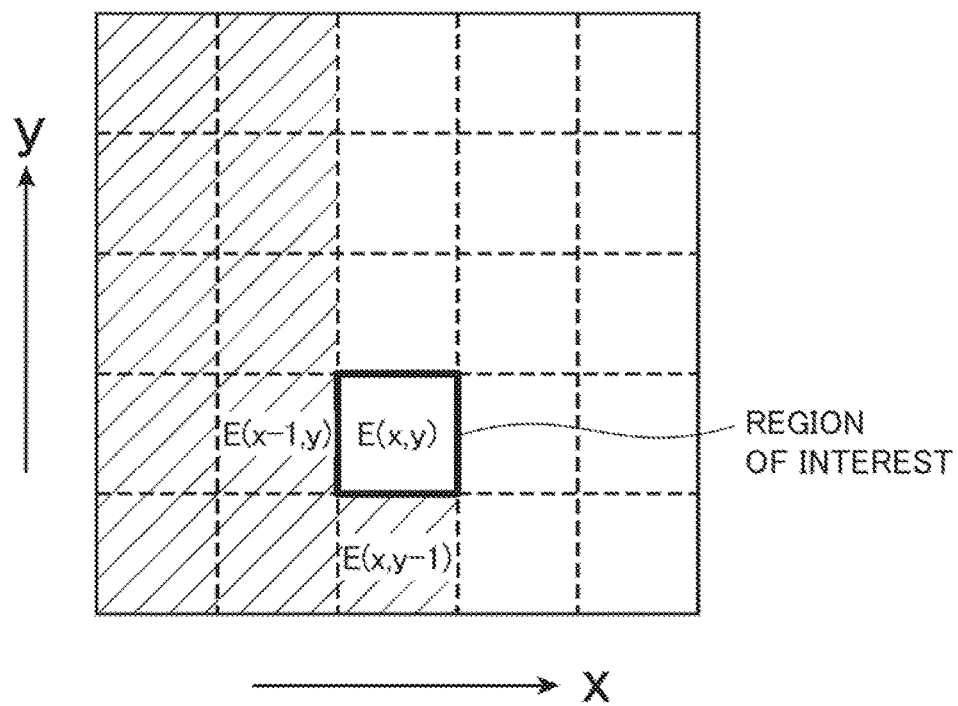
FIG. 3 is a schematic diagram illustrating a region of interest and nearby regions.

FIG. 3 is a diagram schematically expressing the set regions. In FIG. 3, the y direction corresponds to a transmitting direction of the ultrasonic waves, and the x direction corresponds to the direction in which the ultrasound elements are arranged.

As indicated by the broken lines in FIG. 3, the regions are set by dividing the image capturing region into a plurality of quadrangular portions.

Although the regions are indicated as being quadrangular in the illustrated example, the shape is not particularly limited thereto, and the regions may be line-shaped regions corresponding to lines that transmit the ultrasonic beams, or may be points corresponding to individual pixels. Each region may be fan-shaped in correspondence with the shape of the image capturing region, in the case of a convex probe, for example. Furthermore, although the regions all have the same size in the illustrated example, the regions are not limited thereto, and the sizes may vary from region to region.

The sizes of the regions that are set are not particularly limited. Although setting smaller regions improves the overall accuracy of the ultrasound image, there is a risk of increased processing time required for determining the sound velocities.

The region setting section 50 supplies information on the set regions to the sound velocity determiner 52 (an element data obtainer 56).

The sound velocity determiner 52 is a section that sequentially determines appropriate sound velocities for the respective regions set by the region setting section 50.

Figure 2:
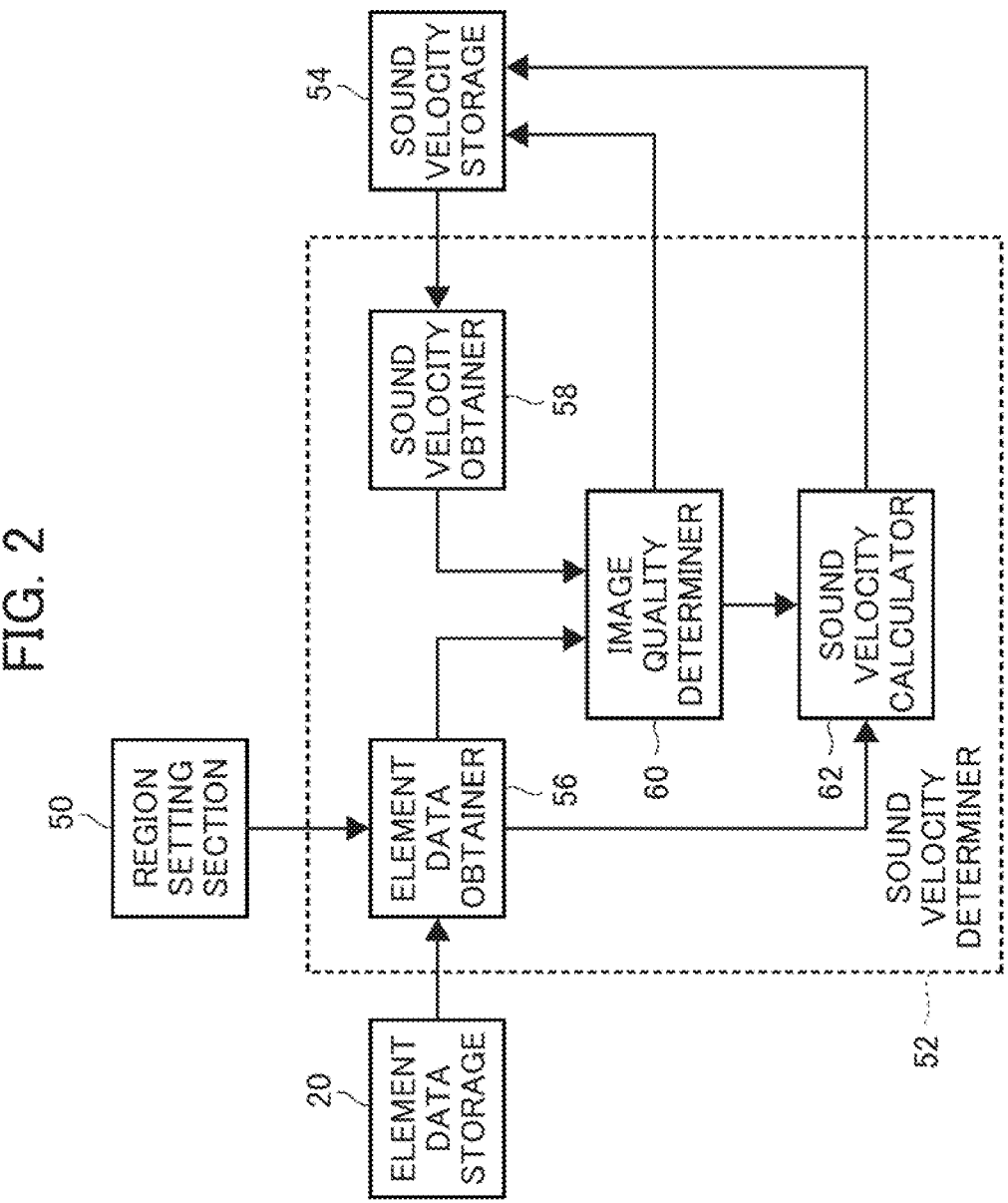
FIG. 2 is a block diagram conceptually illustrating an example of the configuration of a sound velocity determiner in the ultrasound inspection apparatus illustrated in FIG. 1.

As illustrated in FIG. 2, the sound velocity determiner 52 has the element data obtainer 56, a sound velocity obtainer 58, an image quality determiner 60, and a sound velocity calculator 62.

In the invention, the sound velocity of a region expresses a sound velocity from the ultrasound probe 12 to a region in the case where it is assumed that the space between the region and the ultrasound probe 12 (the transducer array 36) is occupied by a homogeneous matter. In other words, the sound velocity is an average sound velocity between the region and the ultrasound probe 12, and this is also referred to as an ambient sound velocity.

The element data obtainer 56 is a section that reads out, from the element data storage 20, element data corresponding to the region for which the sound velocity is to be found (hereinafter, also referred to as a region of interest), based on information on the regions set by the region setting section 50.

The element data obtainer 56 supplies the read-out element data to the image quality determiner 60.

The sound velocity obtainer 58 is a section that reads out, from the sound velocity storage 54, already-determined sound velocities of regions within a predetermined range from, or in other words, regions that are spatially near to, the region for which the sound velocity is to be found (the region of interest), based on the information on the regions set by the region setting section 50, and obtains a preliminary sound velocity as a provisional sound velocity value of the region of interest.

Specifically, in the example illustrated in FIG. 3, assuming that the region of interest for which the sound velocity is to be found is $E_{(x, y)}$ and that the regions indicated by the diagonal lines (the regions x-2 and x-1 as well as $E_{(x, y-1)}$) are regions within the same frame for which the sound velocities have already been determined, the sound velocity obtainer 58 obtains, from the sound velocity storage 54, the sound velocity value of the region $E_{(x, y-1)}$ that is adjacent to the region of interest $E_{(x, y)}$ as the preliminary sound velocity of the region of interest $E_{(x, y)}$.

Note that the sound velocity obtainer 58 is not limited to a configuration that obtains the sound velocity value of the region $E_{(x, y-1)}$ adjacent to the region of interest $E_{(x, y)}$ in the y direction (the ultrasonic wave transmitting direction) as the preliminary sound velocity, and may instead obtain the sound velocity value of a region $E_{(x-1, y)}$ adjacent to the region of interest $E_{(x, y)}$ in the x direction as the preliminary sound velocity. Furthermore, the region from which to obtain the preliminary sound velocity is not limited to a region adjacent to the region of interest, and may be any region within a predetermined range from the region of interest (a nearby region).

Although this predetermined range may be determined in accordance with the diagnosis subject (the type of organ to be inspected) or the like, it is preferable for the predetermined region to be a region within a range of 10 cm from the region of interest, for example. This predetermined region may be set to be changeable by the operator.

Furthermore, the configuration is not limited to obtaining the sound velocity value of one region as the preliminary sound velocity, and the configuration may be such that the sound velocity values of two or more regions are read out and an average of those values, a weighted average of those values, or the like is obtained as the preliminary sound velocity. For example, in FIG. 3, an average of the sound velocity value of the region $E_{(x, y-1)}$ and the sound velocity value of the region $E_{(x-1, y)}$ may be taken as the preliminary sound velocity of the region of interest $E_{(x, y)}$.

In addition, the sound velocity obtainer 58 is not limited to a configuration that obtains the sound velocity value of a region in the same frame as the preliminary sound velocity, and may have a configuration that obtains the sound velocity value of a region in the same position in a frame a predetermined number of frames before as the preliminary sound velocity, or in other words, a configuration that obtains the sound velocity value of a region that is temporally nearby as the preliminary sound velocity.

Figure 4:
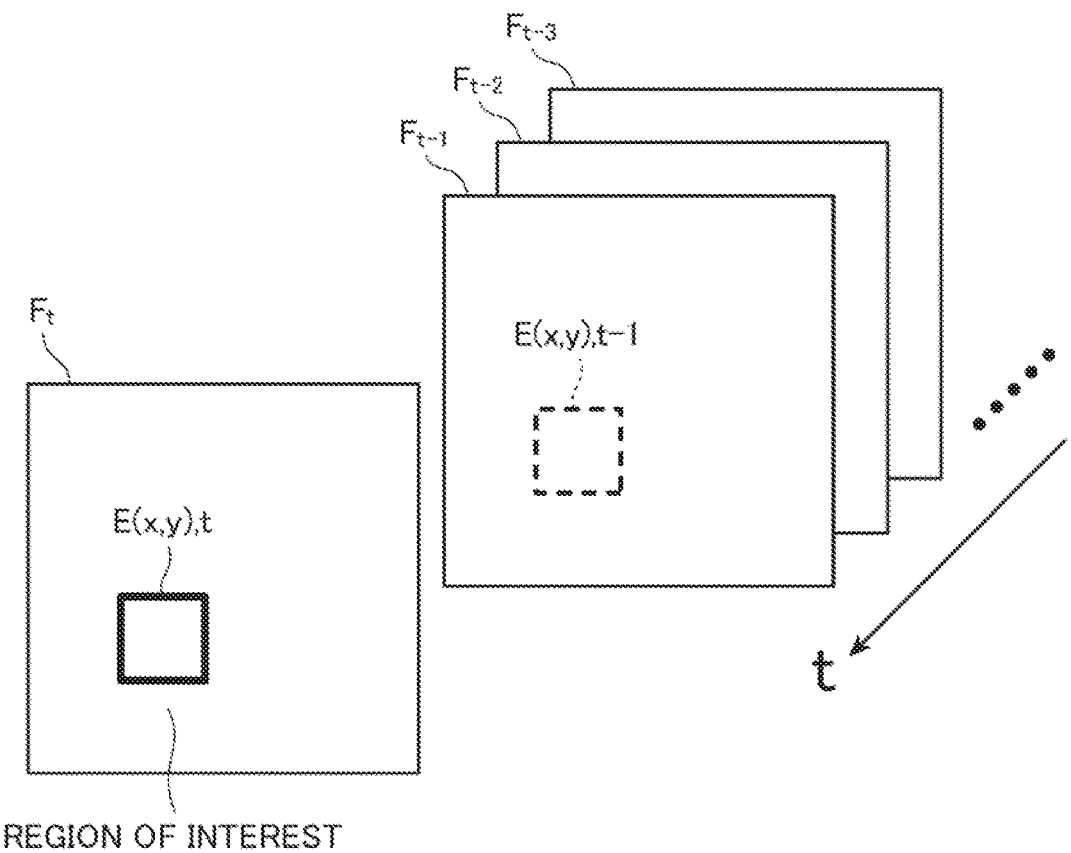
FIG. 4 is a schematic diagram illustrating a region of interest and nearby regions.

FIG. 4 is a schematic diagram illustrating the region of interest and temporally nearby regions.

In FIG. 4, assuming a frame containing the region of interest $E_{(x, y), t}$ for which the sound velocity value is to be found is a frame of interest $F_t$, the sound velocity obtainer 58 may set the preliminary sound velocity of the region of interest $E_{(x, y), t}$ by reading out the sound velocity value of a region $E_{(x, y), t-1}$ in the same position as the region of interest $E_{(x, y), t}$ in a frame $F_{t-1}$ immediately previous to the frame of interest $F_t$.

Note that in the case where the sound velocity value of a region temporally nearby is read out, the frame is not limited to an immediately previous frame, and the preliminary sound velocity of the region of interest $E_{(x, y), t}$ may be set by reading out the sound velocity value of a region in the same position in a frame several frames before (a frame $F_{t-2}$, $F_{t-3}$, or the like). In addition, the sound velocity values of respective regions in a plurality of frames may be read out, and the average value thereof may be taken as the preliminary sound velocity of the region of interest $E_{(x, y), t}$.

In addition, the sound velocity obtainer 58 may read out the sound velocity value of a region temporally nearby and the sound velocity value of a region spatially nearby and take the average value thereof as the preliminary sound velocity of the region of interest. For example, the sound velocity values in a region $E_{(x, y-1), t}$ and a region $E_{(x-1, y), t}$ in the same frame and a region $E_{(x, y), t-1}$ in the previous frame may be read out, and the average value thereof may be taken as the preliminary sound velocity of the region of interest $E_{(x, y), t}$.

The sound velocity obtainer 58 supplies the obtained preliminary sound velocity to the image quality determiner 60.

The image quality determiner 60 is a section that, based on the preliminary sound velocity obtained by the sound velocity obtainer 58, generates an image of the region of interest (an image of interest) from the element data for the region of interest obtained by the element data obtainer 56 and determines the image quality of the image of interest.

The image quality determiner 60 first generates an image of the region of interest from the supplied element data. The method for generating the image is basically the same as that of the image generator 24. That is, in accordance with a reception delay pattern based on the preliminary sound velocity obtained by the sound velocity obtainer 58, a reception focusing process is carried out by delaying and adding the element data, thereby generating reception data (a sound ray signal). Correction for attenuation based on the depth is carried out on the generated sound ray signal, and an envelope detection process is then carried out, thereby generating B-mode image data.

Next, the image quality is determined by evaluating a sharpness value of the generated B-mode image data of the region of interest. The image quality is determined to be good when the sharpness value is no less than a predetermined threshold value, and the image quality is determined to be poor when the sharpness value is less than the threshold value.

Note that a known calculation method may be used as the method for calculating the sharpness value of the image, and for example, a calculation method that calculates a half width of a maximum brightness point in the region of interest as the sharpness value can be used.

Note that the method for determining the image quality carried out by the image quality determiner 60 is not limited to a determination based on the sharpness value, and the image quality may be determined based on an evaluation index such as a contrast or brightness value, a spatial frequency of the image, an integration value, a square integration value, a peak value, a half width, a frequency-spectral integration, a frequency-spectral integration value or square integration value as normalized with its maximum value or a direct current component, or an autocorrelation value.

Furthermore, the method for determining the image quality carried out by the image quality determiner 60 is not limited to the configuration that compares the sharpness value of the image (an evaluation index) with a predetermined threshold value, and may instead employ a configuration that makes a comparison with the sharpness value of the image in the same region in the previous frame and determines that the image quality is good when the difference is within a predetermined range.

In addition, rather than the image of the region of interest, the image quality determiner 60 can determine the image quality based on the reception data on which the reception focusing process has carried out by delaying and adding the element data in accordance with the reception delay pattern based on the preliminary sound velocity obtained by the sound velocity obtainer 58. Specifically, a similarity between a reference signal in which post-phasing addition reception data at the preliminary sound velocity is arranged for the same amount of reception elements as before the phasing addition and pre-phasing addition reception data whose delay time has been corrected according to the preliminary sound velocity (element data of which the delay time is corrected) is evaluated, and the image quality is determined to be good when the similarity is no less than a predetermined threshold value and is determined to be poor when the similarity is less than the threshold value.

In the case where a result of the image quality determination of the region of interest indicates that the image quality is good, the image quality determiner 60 employs the preliminary sound velocity used for the image quality determination as the sound velocity of the region of interest and supplies the preliminary sound velocity to the sound velocity storage 54, whereas in the case where the determination result indicates that the image quality is poor, the image quality determiner 60 supplies the determination result to the sound velocity calculator 62.

The sound velocity calculator 62 is a section that precisely calculates the sound velocity of the region of interest whose image quality has been determined to be poor as a result of the image quality determination carried out by the image quality determiner 60.

When a determination result indicating that the image quality is poor is supplied from the image quality determiner 60, the sound velocity calculator 62 obtains the element data corresponding to the region of interest obtained by the element data obtainer 56. Then, varying the sound velocity value (hereinafter, referred to as set sound velocity) of that element data, the sound velocity calculator 62 forms, based on the respective set sound velocities, ultrasound images by carrying out the reception focusing process, and calculates a set sound velocity at which the contrast and/or sharpness of the image is highest as an optimal sound velocity value of the region of interest.

A method for determining the optimal sound velocity value such as that disclosed in JP 08-317926 A, for example, can be used, where the optimal sound velocity value is determined based on the contrast of the image, a spatial frequency in a scanning direction, a variance, or the like.

Figure 5:
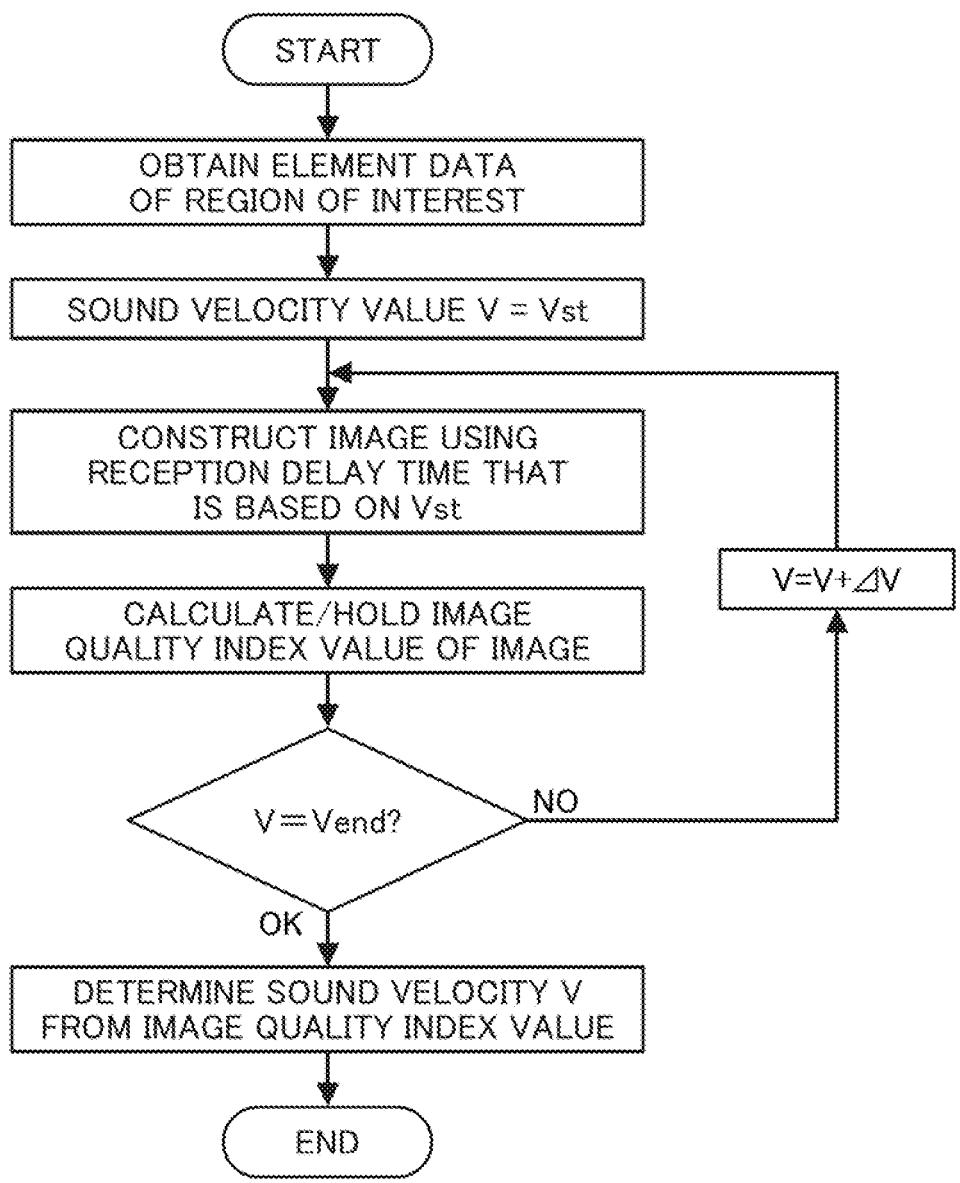
FIG. 5 is a flowchart illustrating the operation of a sound velocity calculator in the ultrasound inspection apparatus illustrated in FIG. 1.

The sound velocity calculator 62 will be described in detail with reference to the flowchart illustrated in FIG. 5.

Upon obtaining the element data of the region of interest, the sound velocity calculator 62 varies a set sound velocity V in intervals of $\Delta V$ from Vst to Vend, and for each set sound velocity V, generates a sound ray signal through the reception focusing process using the element data of the region of interest supplied from the element data obtainer 56 based on that set sound velocity V. The sound velocity calculator 62 then forms an ultrasound image from the sound ray signal and calculates the sharpness of the image of the region of interest at each set sound velocity V.

The sharpness values of the image at respective set sound velocities V are compared, and the set sound velocity V whose obtained sharpness value is the highest is employed as the optimal sound velocity value.

Note that a search range for the set sound velocity V may be set with Vst at approximately 1400 m/s, Vend at approximately 1700 m/s, and $\Delta V$ at approximately 10 to 50 m/s.

The sound velocity calculator 62 supplies the calculated sound velocity value to the sound velocity storage 54.

Note that the sound velocity calculator is not limited to a configuration that takes the set sound velocity at which the sharpness value is highest as the optimal sound velocity value, and may take the set sound velocity at which the image quality is best, based on a contrast or brightness value or an evaluation index such as the spatial frequency of the image, as the optimal sound velocity value.

Furthermore, although the aforementioned example describes a configuration in which the sound velocity calculator 62 searches the set sound velocities within a predetermined search range, the sound velocity calculator 62 is not limited to the configuration, and the sound velocity calculator 62 may be configured to determine the search range using the preliminary sound velocity obtained by the sound velocity obtainer 58 as a reference. For example, the optimal sound velocity may be found using a range of ±50 m/s of the preliminary sound velocity as the search range. Furthermore, in the case where, after the search range is determined using the preliminary sound velocity as a reference and the search is carried out, the image quality determination is carried out and the result is negative, the search range may be expanded and then the optimal sound velocity may be found.

Meanwhile, the method by which the sound velocity calculator 62 calculates the sound velocity is not limited to a configuration in which the sound velocity value at which the image quality is best is found by sequentially varying the set sound velocity within a predetermined search range. Various types of methods for calculating the optimal sound velocity value on a region-by-region basis can be employed. For example, a method in which a similarity between a reference signal in which post-phasing addition reception data at each set sound velocity is arranged for the same amount of reception elements as before the phasing addition and pre-phasing addition reception data whose delay time has been corrected at each set sound velocity (element data of which the delay time is corrected) is evaluated at each set sound velocity, and the sound velocity at which the similarity is highest is taken as the optimal sound velocity value, can be used (this method is disclosed in JP 2012-120242 A).

As described earlier, in the conventional ultrasound inspection apparatus, in order to obtain a higher-quality image, an index (focusing index or the like) for determining the image quality in an exhaustive manner in each of regions (pixels, lines) is obtained based on a plurality of set sound velocities, and the set sound velocity at which the determination result for the image quality is best is then found as the optimal sound velocity value. Accordingly, there has been a problem in that it takes time to find the optimal sound velocities for all of the regions. There is a further problem in that this causes a drop in the frame rate as well.

As opposed to this, according to the invention, a preliminary sound velocity is obtained based on the sound velocity values of regions within a predetermined range from the region of interest, the image quality in the case where an image of the region of interest is generated based on the preliminary sound velocity is determined, and when the determination result for the image quality is positive, the preliminary sound velocity is employed as the sound velocity of the region of interest. It is therefore not necessary to obtain an index for determining the image quality in an exhaustive manner using a plurality of set sound velocities and then find the set sound velocity at which the determination result is best. As such, the appropriate sound velocity value can be found for each region in a short amount of time.

Meanwhile, because the optimal sound velocity value depends on the distance (depth) from the ultrasound probe, the property of a tissue through which the ultrasonic wave passes, and the like, it is highly probable that regions near to each other have similar optimal sound velocity value. Accordingly, a high-quality image can be obtained even when the sound velocity value of a region spatially nearby is employed as the sound velocity of the region of interest.

Meanwhile, in the case where the operator desires to obtain an ultrasound image, the operator holds the ultrasound probe still and obtains the ultrasound image. In such a case, the same tissue is detected in the same region from frame to frame, and thus the optimal sound velocity value also takes on the same value. Accordingly, a high-quality image can be obtained even when the sound velocity value of a region temporally nearby is employed as the sound velocity value of the region of interest.

Furthermore, when a border position between tissues is moved, or when the ultrasound probe is moved by the operator, the determination for the image quality based on the preliminary sound velocity will have a negative result, and when the determination for the image quality based on the preliminary sound velocity obtained from a nearby region has a negative result, then the optimal sound velocity is found; thus, a high-quality image can ultimately be obtained.

As described thus far, the ultrasound inspection apparatus according to the invention can find the appropriate sound velocity value of each region in a short amount of time, and can construct a highly-accurate ultrasound image without causing a drop in the frame rate.

The sound velocity storage 54 stores the sound velocity value supplied from the image quality determiner 60 and the sound velocity calculator 62 in association with region position information, or in other words, as a sound velocity map.

The sound velocity storage 54 may be configured to sequentially update the sound velocity value of a corresponding region each time a sound velocity value is supplied from the image quality determiner 60 or the sound velocity calculator 62, or may generate a sound velocity map on a frame-by-frame basis.

Meanwhile, when the sound velocity obtainer 58 reads out the sound velocity values of regions temporally nearby, the sound velocity storage 54 generates the sound velocity map on a frame-by-frame basis and stores not just the latest sound velocity (sound velocity map), but rather the sound velocity maps of up to several frames before.

The sound velocity storage 54 supplies the information on the sound velocity map to the phasing addition section 38 and the sound velocity obtainer 58.

The controller 30 controls each section in the ultrasound inspection apparatus 10 in accordance with an instruction inputted through the operating section 32 by the operator.

Here, when the operator inputs various types of information through the operating section 32, and particularly information necessary for the region setting section 50 to set the regions and information necessary for the sound velocity determiner 52 to determine the sound velocity, the controller 30 supplies the stated various types of information inputted through the operating section 32 to the transmitter 14, the receiver 16, the element data storage 20, the image generator 24, the display controller 26, the region setting section 50, the sound velocity determiner 52, and the like as necessary.

The operating section 32 is a section for the operator to make input operations, and can be constituted by a keyboard, a mouse, a trackball, a touch panel, or the like.

The operating section 32 has an input device through which the operator performs operations for inputting various types of information as necessary, in particular the aforementioned information used in the setting of regions, the information used in the sound velocity determination, and the like.

The storage unit 34 stores the various types of information inputted through the operating section 32, information necessary for processes and operations of the respective sections controlled by the controller 30, the sections including the transmitter 14, the receiver 16, the element data storage 20, the image generator 24, the display controller 26, the region setting section 50, the sound velocity determiner 52, and the like. In addition, the storage unit 34 stores operating programs, processing programs, and the like for causing the respective sections to execute processes, operations, and the like. A recording medium such as a hard disk, a flexible disk, a magneto-optical disc (MO), a magnetic tape (MT), a random access memory (RAM), a compatible disc read only memory (CD-ROM), a digital versatile disc read only memory (DVD-ROM), or the like can be used as the storage unit 34.

Although the phasing addition section 38, the detection processor 40, the DSC 42, the image creating section 44, the sound velocity obtainer 58, the image quality determiner 60, the sound velocity calculator 62, and the display controller 26 are constituted by a central processing unit (CPU) and an operating program for causing the CPU to carry out various types of processes, those sections may instead be constituted by digital circuitry.

The operation and effect of the ultrasound inspection apparatus illustrated in FIG. 1 will be described to explain the signal processing method of the invention.

First, the operation of the ultrasound inspection apparatus 10 for generating an ultrasound image will be described.

When the operator brings the ultrasound probe 12 into contact with the surface of the subject and starts measurement, an ultrasonic beam is transmitted from the transducer array 36 in accordance with a driving signal supplied from the transmitter 14. Then the transducer array 36 receives an ultrasonic echo from the subject and outputs an analog element signal as a reception signal.

The receiver 16 outputs a single piece of analog element data constituted by the analog element signals outputted from the respective elements to supply the analog element data to the A/D converter 18. The A/D converter 18 converts the analog element data into digital element data and supplies the digital element data to the element data storage 20 to cause the digital element data to be stored.

The phasing addition section 38 of the image generator 24 reads out the element data from the element data storage 20, generates reception data (sound ray signal) by carrying out a reception focusing process on the element data, and supplies the reception data to the detection processor 40. At this time, the phasing addition section 38 carries out the reception focusing process based on the sound velocity map stored in the sound velocity storage 54. The detection processor 40 generates the B-mode image signal by processing the sound ray signal. The DSC 42 raster-converts the B-mode image signal, and the image creating section 44 carries out image processing, thereby generating the ultrasound image. The generated ultrasound image is stored in the image memory 46 and is displayed in the monitor 28 by the display controller 26.

Next, the operation of the ultrasound inspection apparatus 10 for obtaining the sound velocity map will be described.

Figure 6:
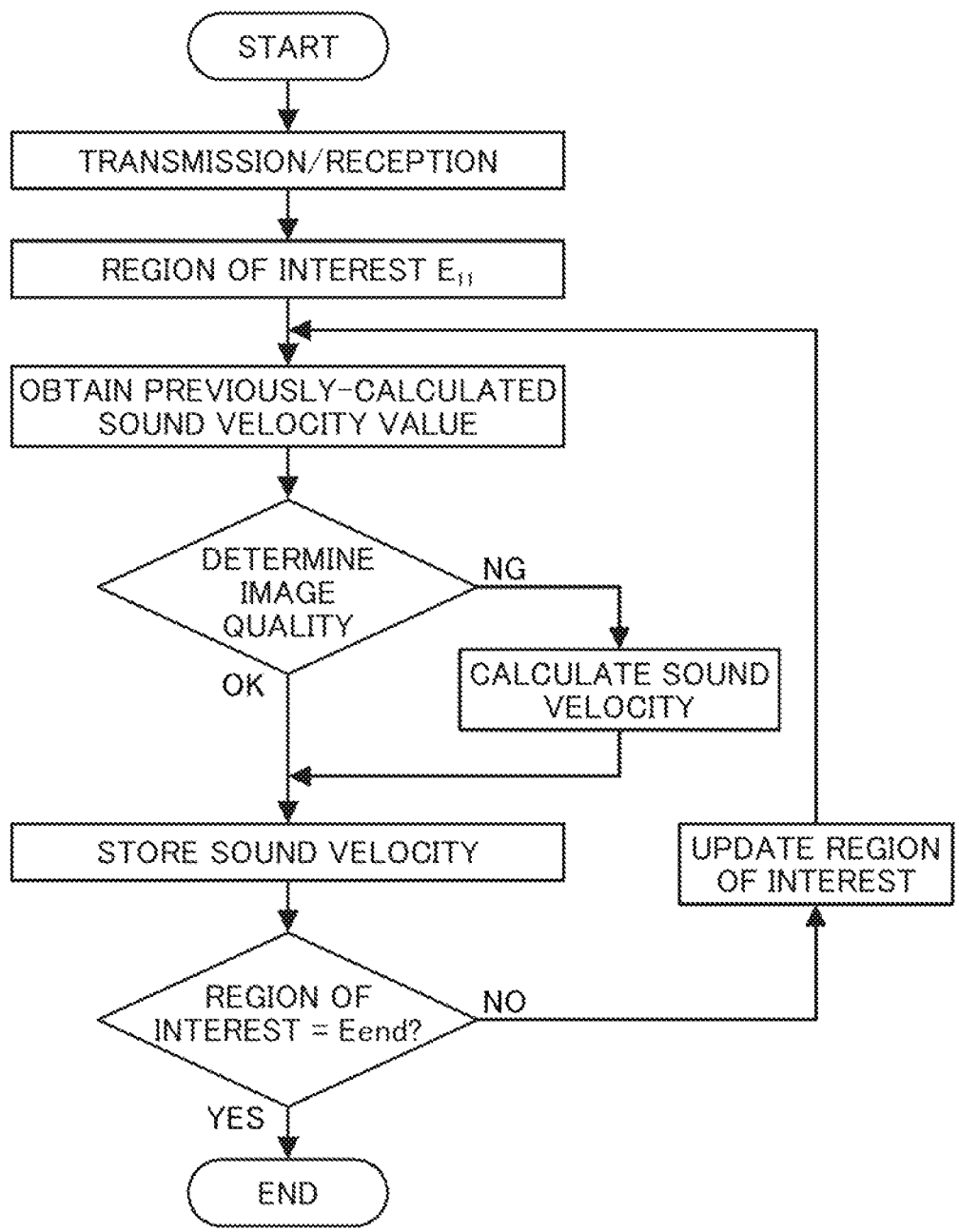
FIG. 6 is a flowchart illustrating the operation of the ultrasound inspection apparatus illustrated in FIG. 1.

FIG. 6 is a flowchart illustrating the operation of the ultrasound inspection apparatus 10 illustrated in FIG. 1.

When the operator brings the ultrasound probe 12 into contact with the surface of the subject and starts measurement, an ultrasonic beam is transmitted from the transducer array 36 in accordance with a driving signal supplied from the transmitter 14. The transducer array 36 receives an ultrasonic echo from the subject and outputs an analog element signal as a reception signal.

The receiver 16 outputs a single piece of analog element data constituted by the analog element signals outputted from the respective elements to supply the analog element data to the A/D converter 18. The A/D converter 18 converts the analog element data into digital element data and supplies the digital element data to the element data storage 20 to cause the digital element data to be stored.

On the other hand, the region setting section 50 sets a plurality of regions in an image capturing region that is to undergo scanning by ultrasonic waves, in response to an input made through the operating section 32 or in response to an instruction from the controller 30.

The sound velocity determiner 52 sequentially determines the sound velocity of each region set by the region setting section 50 (from $E_{11}$ to $E_{end}$).

The element data obtainer 56 of the sound velocity determiner 52 reads out, from the element data storage 20, the element data corresponding to the region of interest and supplies the element data to the image quality determiner 60. Meanwhile, the sound velocity obtainer 58 reads out the already-determined sound velocity of a region near the region of interest from the sound velocity storage 54, obtains that sound velocity as the preliminary sound velocity, and supplies the preliminary sound velocity to the image quality determiner 60.

The image quality determiner 60 first carries out the reception focusing process on the element data of the region of interest obtained by the element data obtainer 56 in accordance with a reception delay pattern that is based on the preliminary sound velocity obtained by the sound velocity obtainer 58 to generate the reception data. Then, the image quality determiner 60 performs correction for attenuation based on the depth and an envelope detection process on the reception data to generate the B-mode image data. Next, the image quality is determined by evaluating the sharpness value of the generated B-mode image data for the region of interest, and when the image quality is determined to be good, the preliminary sound velocity used in the image quality determination is employed as the sound velocity of the region of interest and supplied to the sound velocity storage 54. When the image quality determination has a negative-result, the determination result is supplied to the sound velocity calculator 62.

When the image quality determination has a negative result, the sound velocity calculator 62 varies the set sound velocity in an exhaustive manner, calculates the sound velocity at which the image quality is best as the sound velocity of the region of interest, and supplies that sound velocity to the sound velocity storage 54.

The sound velocity storage 54 stores the sound velocity value supplied from the image quality determiner 60 and the sound velocity calculator 62 in association with region position information, as a sound velocity map.

Thus, according to the ultrasound inspection apparatus of the first embodiment of the invention, a preliminary sound velocity is obtained based on the sound velocity values of regions within a predetermined range from the region of interest, the image quality in the case where an image of the region of interest is generated based on the preliminary sound velocity is determined, and when the determination result for the image quality is positive, the preliminary sound velocity is employed as the sound velocity of the region of interest. It is therefore not necessary to obtain an index for determining the image quality in an exhaustive manner using a plurality of set sound velocities and then find the set sound velocity at which the determination result is best. As such, the appropriate sound velocity value can be found for each region in a short amount of time.

Meanwhile, because the optimal sound velocity value depends on the distance (depth) from the ultrasound probe, the form of a tissue through which the ultrasonic wave passes, and the like, it is highly probable that regions near to each other have similar optimal sound velocity value. Accordingly, a high-quality image can be obtained even when the sound velocity value of a region spatially nearby is employed as the sound velocity of the region of interest.

Meanwhile, in the case where the operator desires to obtain an ultrasound image, the operator holds the ultrasound probe still and obtains the ultrasound image. In such a case, the same tissue is detected in the same region from frame to frame, and thus the optimal sound velocity value also takes on the same value. Accordingly, a high-quality image can be obtained even when the sound velocity value of a region temporally nearby is employed as the sound velocity value of the region of interest.

Furthermore, when a border position between tissues is moved, or when the ultrasound probe is moved by the operator, the image quality determination based on the preliminary sound velocity will have a negative result, and when the image quality determination based on the preliminary sound velocity obtained from a nearby region has a negative result, the optimal sound velocity is obtained; thus, a high-quality image can ultimately be obtained.

As described thus far, the ultrasound inspection apparatus according to the invention can find the appropriate sound velocity value of each region in a short amount of time, and can construct a highly-accurate ultrasound image without causing a drop in the frame rate.

Although the foregoing example describes a configuration in which the image quality determiner 60 generates an image of the region of interest and evaluates the image quality by obtaining an evaluation index (a sharpness value or the like) based on the image, the invention is not limited thereto, and the image quality may be determined from the element data of the region of interest without generating the image of the region of interest. In other words, the configuration may be such that a focus index is obtained by carrying out the reception focusing process on the element data for each of a plurality of set sound velocities, and the optimal sound velocity is determined based on the focus index.

The method disclosed in JP 2011-92686 A, for example, can be used as the method for calculating and determining the focus index.

In addition, although the foregoing example describes a configuration in which the image quality determiner 60 has a function for generating an image for determining the image quality, the invention is not limited thereto, and the configuration may be such that the image generator 24 generates an image for image quality determination and the image quality determiner 60 then carries out the determination.

Furthermore, the configuration is not limited to determining the image quality by obtaining the preliminary sound velocity of all of the regions in a single frame. A pre-set initial value may be used as the preliminary sound velocity for the region for which the sound velocity is first determined in a single frame, or the optimal sound velocity may be calculated by the sound velocity calculator 62 without obtaining the preliminary sound velocity (without determining the image quality). Furthermore, in some predetermined regions, the sound velocity calculator 62 may calculate the optimal sound velocity without obtaining the preliminary sound velocity and carrying out the image quality determination. For example, by calculating the optimal sound velocity for a region that contains the focal point of the ultrasonic beam, the optimal sound velocity can be found more accurately, and by using the calculated sound velocity as the preliminary sound velocity, the image quality of the regions in the periphery of the stated region can be improved.

Meanwhile, the ultrasound image generation and sound velocity determination may be carried out simultaneously or individually. In other words, the sound velocity may be determined and the ultrasound image may be generated from element data obtained through transmission and reception of a single set of ultrasonic waves for a single frame, or the ultrasound image generation and sound velocity determination may be individually carried out using element data obtained by separate transmissions and receptions. In the case of a configuration in which the ultrasound image is generated from the element data used to determine the sound velocity, the image used to determine the image quality may be used as the ultrasound image for regions in which the determination result made by the image quality determiner is positive.

In addition, the sound velocity determination may be carried out on a frame-by-frame basis or once in several frames.

Although the foregoing example describes a configuration in which the reception focusing process is carried out based on the sound velocity map stored in the sound velocity storage 54 at the time of carrying out the reception focusing process on the element data, the configuration is not limited thereto, and the delay amount of the driving signal may be adjusted based on the sound velocity map stored in the sound velocity storage 54 when the ultrasonic beams are transmitted by the transmitter 14 as well.

In addition, although the foregoing example describes a configuration in which the preliminary sound velocity is obtained and the image quality is determined, and the sound velocity calculator 62 calculates the optimal sound velocity of the region of interest when the determination result is negative, the configuration is not limited thereto. The configuration may be such that the determination result is displayed in the monitor 28 to warn the operator when the determination result is negative. In this case, whether or not to calculate the sound velocity may be determined by the operator.

As described earlier, the region used by the sound velocity obtainer 58 for obtaining the preliminary sound velocity may be any region as long as the region is temporally or spatially near the region of interest. Which region is used to obtain the sound velocity value may be determined in advance, or may be determined automatically. For example, it is preferable to detect movement of the ultrasound probe 12 using an accelerometer, a difference from an image in the previous frame, or the like, and to obtain the sound velocity value of a region temporally nearby in the case where the ultrasound probe 12 is held still. Meanwhile, in the case where a feature quantity of the image varies from frame to frame, it is preferable to obtain the sound velocity value of a region spatially nearby, and among the regions to the left and right of, and above and under the region of interest, which region is used to obtain the sound velocity may be automatically determined based on the direction of the movement.

In addition, the image capturing region may be divided into a plurality of partial images based on an image feature quantity or the like, and the sound velocity value of a region within the same partial image may be obtained as the preliminary sound velocity.

Next, a second embodiment of the ultrasound inspection apparatus according to the invention will be described.

Figure 7:
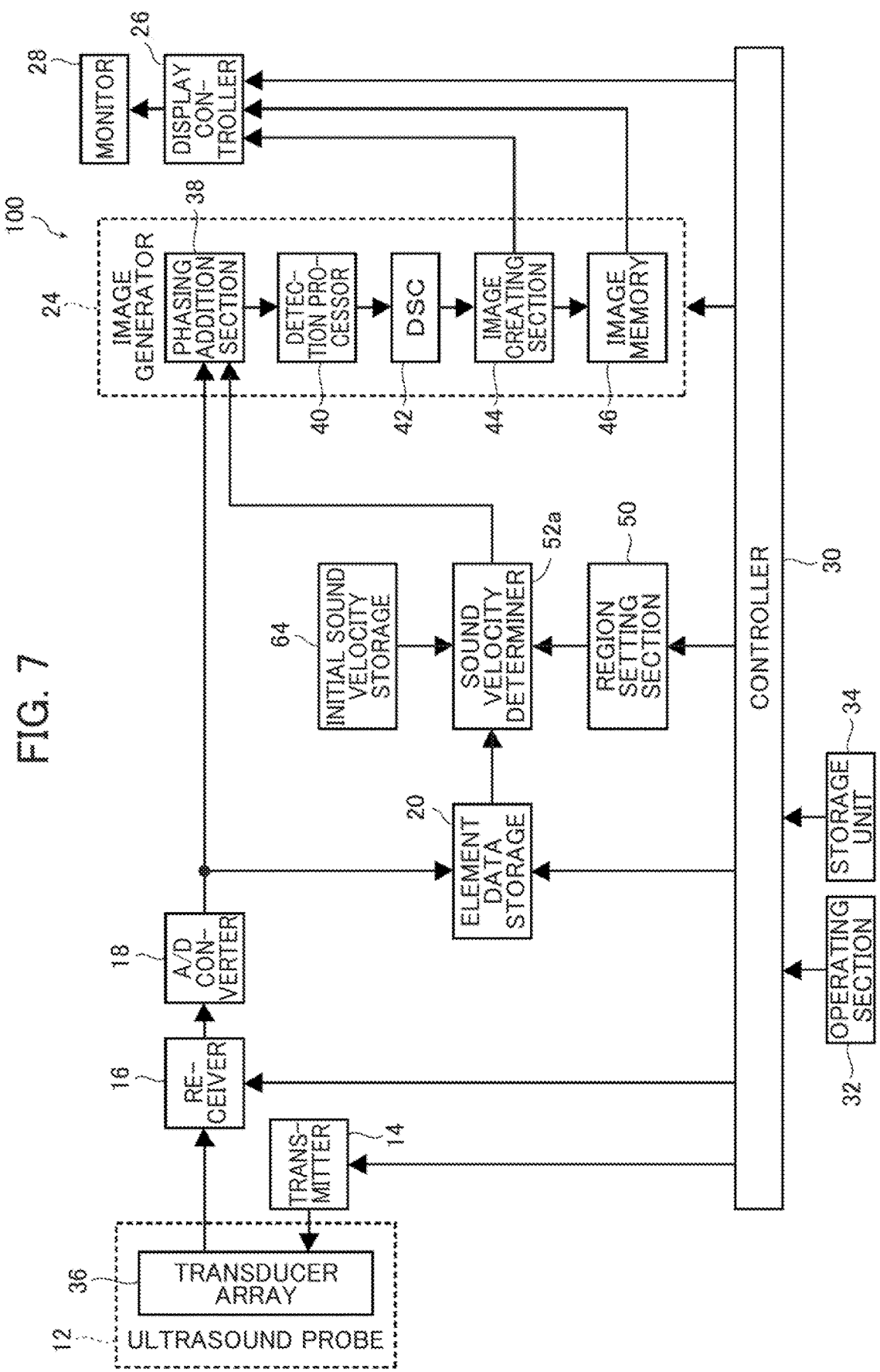
FIG. 7 is a block diagram conceptually illustrating an example of the configuration of a second embodiment of the ultrasound inspection apparatus according to the invention.

FIG. 7 is a block diagram conceptually illustrating an example of the configuration of the second embodiment of the ultrasound inspection apparatus according to the invention.

Aside from having a sound velocity determiner 52a instead of the sound velocity determiner 52, not having the sound velocity storage 54, and having an initial sound velocity storage 64, an ultrasound inspection apparatus 100 illustrated in FIG. 7 has the same configuration as the ultrasound inspection apparatus 10 illustrated in FIG. 1. As such, identical constituent elements will be given the same reference numerals, and detailed descriptions thereof will be omitted.

As illustrated in FIG. 7, the ultrasound inspection apparatus 100 includes the ultrasound probe 12, the transmitter 14 and the receiver 16 connected to the ultrasound probe 12, the A/D converter 18, the element data storage 20, the image generator 24, the display controller 26, the monitor 28, the controller 30, the operating section 32, the storage unit 34, the region setting section 50, the sound velocity determiner 52a, and the initial sound velocity storage 64.

The initial sound velocity storage 64 is a section that stores an initial sound velocity, which is a pre-set predetermined sound velocity value to be used by the sound velocity determiner 52 to determine the sound velocity of each region.

It is preferable for the initial sound velocity stored in the initial sound velocity storage 64 to be a value close to the sound velocity value in a living body, namely within a range of 1400 to 1700 m/s, and particularly within a range of 1450 to 1550 m/s.

Note that it is sufficient for the initial sound velocity storage 64 to store at least one initial sound velocity value, but an appropriate initial sound velocity value may be stored for each diagnosis region (each type of organ).

The initial sound velocity storage 64 supplies information on an initial sound velocity to a sound velocity obtainer 58a in the sound velocity determiner 52a.

Figure 8:
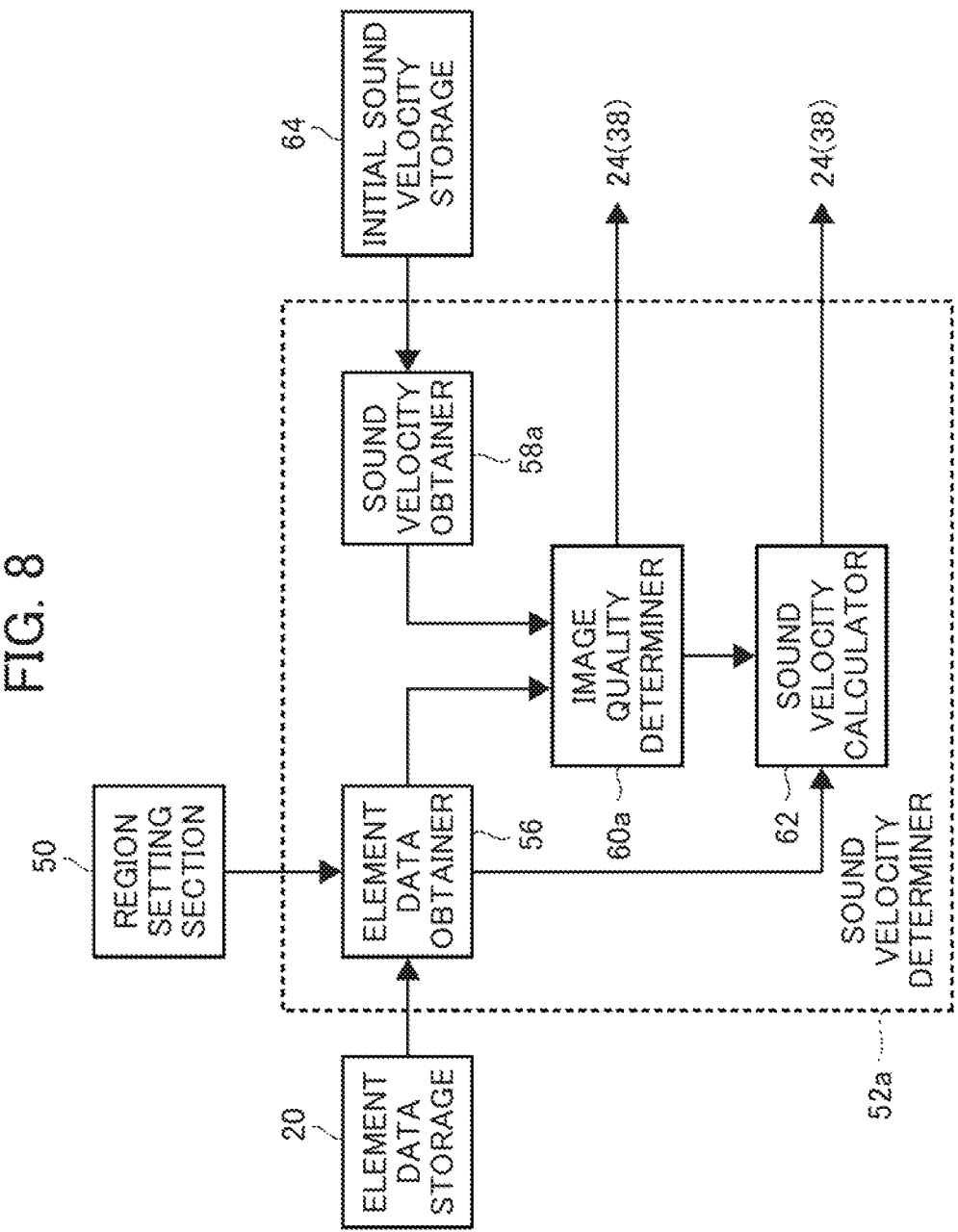
FIG. 8 is a block diagram conceptually illustrating an example of the configuration of a sound velocity determiner in the ultrasound inspection apparatus illustrated in FIG. 7.

As illustrated in FIG. 8, the sound velocity determiner 52a has the element data obtainer 56, the sound velocity obtainer 58a, an image quality determiner 60a, and the sound velocity calculator 62.

The sound velocity obtainer 58a is a section that reads out the initial sound velocity value stored in the initial sound velocity storage 64 as the preliminary sound velocity.

When having a single initial sound velocity value stored therein, the initial sound velocity storage 64 may obtain that initial sound velocity as the preliminary sound velocity. Furthermore, when having a plurality of initial sound velocity values stored therein, the initial sound velocity storage 64 may select and obtain an appropriate initial sound velocity value based on information inputted through the operating section 32, information on a pre-set diagnosis region, or the like.

The sound velocity obtainer 58 supplies the obtained initial sound velocity value to the image quality determiner 60a.

Like the image quality determiner 60, the image quality determiner 60a is a section that, based on the preliminary sound velocity obtained by the sound velocity obtainer 58a, generates an image of the region of interest (an image of interest) from the element data of the region of interest obtained by the element data obtainer 56.

Next, like the image quality determiner 60, the image quality determiner 60a determines the image quality by evaluating a sharpness value of the generated B-mode image data of the region of interest. The image quality is determined to be good when the sharpness value is no less than a predetermined threshold value, and the image quality is determined to be poor when the sharpness value is less than the threshold value.

An example of the image quality determination performed by the image quality determiner 60a will be described with reference to FIG. 9.

In FIG. 9, the image capturing region is set with 5 by 5 regions, as one example. The image quality determiner 60a determines the image quality for each region, and whether the determination result for each region is positive (OK) or negative (NG) is determined. The sound velocity calculator 62 precisely calculates the sound velocities of the regions determined as NG (that is, regions (2, 3) to (2, 5) and (3, 3) to (3, 5)) as a result of the image quality determination, as illustrated in the drawing.

For a region of interest whose image quality has been determined to be poor as a result of the image quality determination performed by the image quality determiner 60a, the sound velocity calculator 62 precisely calculates the sound velocity and supplies the calculated sound velocity value to the phasing addition section 38 of the image generator 24 as the sound velocity value of the region of interest.

Thus, according to the second embodiment of the invention, the image quality in the case where an image is generated based on the pre-set initial sound velocity value is determined for each of a plurality of set regions, and when the image quality determination result is positive, the initial sound velocity value is employed as the sound velocity of the corresponding region. It is therefore not necessary to obtain an index for determining the image quality in an exhaustive manner using a plurality of set sound velocities and then find the set sound velocity at which the determination result is best, and as such the appropriate sound velocity value can be found for each region in a short amount of time.

In addition, in the case where the image quality determination result based on the initial sound velocity is negative, then the optimal sound velocity of the corresponding region is found, and thus a high-quality image can be obtained.

As described thus far, the ultrasound inspection apparatus according to the invention can find the appropriate sound velocity value of each region in a short amount of time, and can construct a highly-accurate ultrasound image without causing a drop in the frame rate.

The operation and effect of the ultrasound inspection apparatus 100 illustrated in FIG. 10 will be described.

First, the region setting section 50 sets a plurality of regions in an image capturing region that is to undergo scanning by ultrasonic waves, in response to an input made through the operating section 32 or in response to an instruction from the controller 30. Meanwhile, the pre-set initial sound velocity is stored in the initial sound velocity storage 64.

When the operator brings the ultrasound probe 12 into contact with the surface of the subject and starts measurement, an ultrasonic beam is transmitted from the transducer array 36 in accordance with a driving signal supplied from the transmitter 14. Then the transducer array 36 receives an ultrasonic echo from the subject and outputs an analog element signal as a reception signal.

The receiver 16 outputs a single piece of analog element data constituted by the analog element signals outputted from the respective elements to supply the data to the A/D converter 18. The A/D converter 18 converts the analog element data into digital element data and supplies the digital element data to the element data storage 20 to cause the digital element data to be stored.

When the element data is stored, the sound velocity determiner 52a determines the sound velocity of each region.

The operation of the sound velocity determiner 52a will be described with reference to the flowchart in FIG. 10.

The sound velocity obtainer 58a of the sound velocity determiner 52a reads out the initial sound velocity stored in the initial sound velocity storage 64 and supplies the initial sound velocity to the image quality determiner 60a. The element data obtainer 56 reads out the element data corresponding to the region whose image quality is to be determined (the region of interest) and supplies the data to the image quality determiner 60a.

The image quality determiner 60a first carries out the reception focusing process on the element data of the region of interest obtained by the element data obtainer 56 in accordance with a reception delay pattern that is based on the initial sound velocity obtained by the sound velocity obtainer 58a to generate the reception data. Then, the image quality determiner 60a performs correction for attenuation based on the depth and an envelope detection process on the reception data to generate the B-mode image data. Next, the image quality is determined by evaluating the sharpness value of the generated B-mode image data for the region of interest, and when the image quality is determined to be good, the initial sound velocity used in the image quality determination is employed as the sound velocity of the region of interest and supplied to the phasing addition section 38 of the image generator 24. When the image quality determination has a negative result, the determination result is supplied to the sound velocity calculator 62.

When the image quality determination has a negative result, the sound velocity calculator 62 varies the set sound velocity in an exhaustive manner, calculates the sound velocity at which the image quality is best as the sound velocity of the region of interest, and supplies that sound velocity to the phasing addition section 38.

The phasing addition section 38 of the image generator 24 reads out the element data from the element data storage 20, and based on the sound velocity of each region supplied from the image quality determiner 60a and the sound velocity calculator 62, selects a reception delay pattern for the element data, generates the reception data (sound ray signal) by carrying out the reception focusing process, and supplies the data to the detection processor 40. The detection processor 40 generates the B-mode image signal by processing the sound ray signal. The DSC 42 raster-converts the B-mode image signal, and the image creating section 44 carries out image processing, thereby generating the ultrasound image. The generated ultrasound image is stored in the image memory 46 and is displayed in the monitor 28 by the display controller 26.

Thus, in the ultrasound inspection apparatus of the second embodiment of the invention, the image quality in the case where an image is generated based on the pre-set initial sound velocity value is determined for each of a plurality of set regions, and when the image quality determination result is positive, the initial sound velocity value is employed as the sound velocity of the corresponding region. It is therefore not necessary to obtain an index for determining the image quality in an exhaustive manner using a plurality of set sound velocities and then find the set sound velocity at which the determination result is best, and as such the appropriate sound velocity value can be found for each region in a short amount of time.

In addition, in the case where the image quality determination result based on the initial sound velocity is negative, then the optimal sound velocity of the corresponding region is found, and thus a high-quality image can be obtained.

As described thus far, the ultrasound inspection apparatus according to the invention can find the appropriate sound velocity value of each region in a short amount of time, and can construct a highly-accurate ultrasound image without causing a drop in the frame rate.

Although the initial sound velocity stored in the initial sound velocity storage 64 is assumed to be pre-set in the foregoing embodiment, the invention is not limited thereto. The initial sound velocity stored in the initial sound velocity storage 64 may be updated as appropriate. For example, an average value of the sound velocities of the respective regions determined by the sound velocity determiner 52a or the like may be set as the initial sound velocity for the next frame.

In addition, there is no particular limitation on the timing at which the stored initial sound velocity is updated. The initial sound velocity may be updated every frame or at intervals of a predetermined number of frames, or the initial sound velocity may be updated in the case where the number of regions whose image quality has been determined to be NG by the image quality determiner 60 has exceeded a predetermined number.

In addition, although the foregoing embodiment describes a configuration in which the image quality determiner 60a has a function for generating an image for determining the image quality, the invention is not limited thereto, and the configuration may be such that the image generator 24 generates an image for image quality determination and the image quality determiner 60a then carries out the determination. In this case, for a region whose image quality has been determined to be NG, the image generator 24 may once again generate an image based on the sound velocity calculated by the sound velocity calculator 62, and the overall ultrasound image may then be generated.

The ultrasound inspection apparatus of each of the foregoing embodiments is controlled with a signal processing program stored in a memory (not illustrated) belonging to the controller. That is, the signal processing program is read out from the memory by the controller, and a function for setting the regions and determining the sound velocity by sequentially determining the image quality for each of the set regions is executed according to the signal processing program. In other words, this memory storing the program is the computer readable recording medium having stored therein the signal processing program for the ultrasound inspection apparatus according to the invention.

Note that the signal processing program of the ultrasound inspection apparatus is not limited to that stored in a memory belonging to the controller in this manner; the configuration may be such that the signal processing program is recorded in a memory medium configured to be detachable with respect to the ultrasound inspection apparatus (a removable medium), such as a CD-ROM, and the program is loaded into the apparatus via an interface compliant with the removable medium. In other words, the recording medium of the invention may be such a removable medium.

Although an ultrasound inspection apparatus, a signal processing method for the ultrasound inspection apparatus, and a computer readable recording medium having stored therein a program for the ultrasound inspection apparatus according to the invention have been described in detail thus far, the invention is not intended to be limited to the foregoing examples, and it goes without saying that various improvements, variations, and the like may be carried out without departing from the gist of the invention.

What is claimed is:

1. An ultrasound inspection apparatus for inspecting an inspection object using an ultrasonic beam, the apparatus comprising a processor,
   to set a plurality of regions within the inspection object,
   to calculate a sound velocity of each of the plurality of regions as a first sound velocity, to take one of the plurality of regions as a first region of interest and further obtain a preliminary sound velocity of the first region of interest, the preliminary sound velocity being different from the first sound velocity of the first region of interest and being obtained based on the first sound velocity of at least one of the plurality of regions temporally and/or spatially within a predetermined distance from the first region of interest, to determine an image quality of the first region of interest based on the preliminary sound velocity, to obtain a second sound velocity of the first region of interest based on a determination result, and to generate an ultrasound image based on the second sound velocity, wherein the processor obtains the preliminary sound velocity as the second velocity when the determination result is positive, and obtains the first velocity as the second velocity when the determination result is negative.

2. The ultrasound inspection apparatus according to claim 1, wherein the one of the plurality of regions spatially within the predetermined distance is a region near the first region of interest in a same image.

3. The ultrasound inspection apparatus according to claim 1, wherein the one of the plurality of regions spatially within the predetermined distance is a region in a same partial image when an image is regionally divided into a plurality of partial images.

4. The ultrasound inspection apparatus according to claim 1, wherein the one of the plurality of regions temporally within the predetermined distance is a region corresponding to the first region of interest in an image of a frame a predetermined number of frames before.

5. The ultrasound inspection apparatus according to claim 1, wherein the one of the plurality of regions temporally within the predetermined distance is a region corresponding to the first region of interest in at least one of images obtained by performing a predetermined process on images of a plurality of frames up to a predetermined number of frames before or a region corresponding to the first region of interest in at least one of the images of the plurality of frames up to the predetermined number of frames before, the sound velocity of at least one of the plurality of regions being a sound velocity obtained by performing a predetermined process on sound velocities of the plurality of frames up to the predetermined number of frames before.

6. The ultrasound inspection apparatus according to claim 5, wherein the predetermined process on sound velocities is a process for obtaining one of an average value and a median value of the sound velocities of the plurality of frames up to the predetermined number of frames before.

7. The ultrasound inspection apparatus according to claim 1, wherein the processor determines the image quality based on one of a sharpness, a brightness, a contrast, and a frequency of an image of the first region of interest generated based on the preliminary sound velocity.

8. The ultrasound inspection apparatus according to claim 1, wherein the processor determines the image quality by comparing the image of the first region of interest generated based on the preliminary sound velocity with an image of a same region in a previous image.

9. The ultrasound inspection apparatus according to claim 1, wherein the processor determines the image quality by evaluating a similarity between reference data generated based on post-phasing addition reception data of the first region of interest generated based on the preliminary sound velocity, and pre-phasing addition reception data.

10. The ultrasound inspection apparatus according to claim 1, further comprising an element data storage configured to store element data which each of elements in a transducer array outputs upon receiving an ultrasonic echo.

11. An ultrasound inspection apparatus for inspecting an inspection object using an ultrasonic beam, the apparatus comprising:
a processor,
to set a plurality of regions within the inspection object,
to calculate a sound velocity of each of the plurality of regions as a first sound velocity,
to take one of the plurality of regions as a first region of interest and further obtain a preliminary sound velocity of the first region of interest, the preliminary sound velocity being different from the first sound velocity of the first region of interest and being obtained based on the first sound velocity of at least one of the plurality of regions temporally and/or spatially within a predetermined distance from the first region of interest,
to determine an image quality of the first region of interest based on the preliminary sound velocity obtained,
to obtain a second sound velocity of the first region of interest based on a determination result, and
to generate an ultrasound image based on the second sound velocity; and
an initial sound velocity storage configured to store a pre-set initial sound velocity,
wherein the processor obtains the preliminary sound velocity as the second velocity when the determination result made is positive, and obtains the first velocity as the second velocity when the determination result is negative.

12. The ultrasound inspection apparatus according to claim 11, wherein the initial sound velocity storage stores a plurality of the initial sound velocities, and the initial sound velocity used in an image quality determination performed by the processor is selected based on an input from an operating section.

13. The ultrasound inspection apparatus according to claim 11, wherein the initial sound velocity stored in the initial sound velocity storage is a value near a sound velocity in a living body.

14. The ultrasound inspection apparatus according to claim 13, wherein the value near the sound velocity in the living body is a value from 1400 to 1700 m/s.

15. The ultrasound inspection apparatus according to claim 11, wherein the initial sound velocity stored in the initial sound velocity storage is set again based on the determination result.

16. A signal processing method for an ultrasound inspection apparatus for inspecting an inspection object using an ultrasonic beam, the method comprising:
a region setting step of setting a plurality of regions within the inspection object;
a first sound velocity calculating step of calculating a sound velocity of each of the plurality of regions as a first sound velocity;
a first sound velocity obtaining step of taking one of the plurality of regions as a first region of interest and further obtaining a preliminary sound velocity of the first region of interest, the preliminary sound velocity being different from the first sound velocity of the first region of interest and being obtained based on the first sound velocity of at least one of the plurality of regions temporally and/or spatially within a predetermined distance from the first region of interest;

an image quality determining step of determining an image quality of the first region of interest based on the preliminary sound velocity obtained in the sound velocity obtaining step, and a second sound velocity obtaining step of obtaining a second sound velocity of the first region of interest based on a determination result, an image generating step of generating an ultrasound image based on the second sound velocity, wherein the preliminary sound velocity obtained in the first sound velocity obtaining step is employed as the second velocity when the determination result made in the image quality determining step is positive, and the first sound velocity calculated in the first sound velocity calculating step is employed as the second velocity when the determination result is negative.

17. A non-transitory computer readable recording medium having stored therein a program that causes a computer to execute signal processing for an ultrasound inspection apparatus for inspecting an inspection object using an ultrasonic beam, the program comprising:

a region setting step of setting a plurality of regions within the inspection object;

a first sound velocity calculating step of calculating a sound velocity of each of the plurality of regions as a first sound velocity;

a first sound velocity obtaining step of taking one of the plurality of regions as a first region of interest and further obtaining a preliminary sound velocity of the first region of interest, the preliminary sound velocity being different from the first sound velocity of the first region of interest and being obtained based on the first sound velocity of at least one of the plurality of regions temporally and/or spatially within a predetermined distance from the first region of interest;

an image quality determining step of determining an image quality of the first region of interest based on the preliminary sound velocity obtained in the sound velocity obtaining step, and a second sound velocity obtaining step of obtaining a second sound velocity of the first region of interest based on a determination result, an image generating step of generating an ultrasound image based on the second sound velocity, wherein the preliminary sound velocity obtained in the first sound velocity obtaining step is employed as the second velocity when the determination result made in the image quality determining step is positive, and the first sound velocity calculated in the first sound velocity calculating step is employed as the second velocity when the determination result is negative.

18. A signal processing method for an ultrasound inspection apparatus for inspecting an inspection object using an ultrasonic beam, the method comprising:

a region setting step of setting a plurality of regions within the inspection object:

a first sound velocity calculating step of calculating a sound velocity of each of the plurality of regions as a first sound velocity;

a first sound velocity obtaining step of taking one of the plurality of regions as a first region of interest and further obtaining a preliminary sound velocity of the first region of interest, the preliminary sound velocity being different from the first sound velocity of the first region of interest and being obtained based on the first sound velocity of at least one of the plurality of regions temporally and/or spatially within a predetermined distance from the first region of interest;

an image quality determining step of determining an image quality of the first region of interest based on the preliminary sound velocity obtained in the sound velocity obtaining step, a second sound velocity obtaining step of obtaining a second sound velocity of the first region of interest based on a determination result, and an image generating step of generating an ultrasound image based on the second sound velocity, wherein the first sound velocity obtaining step obtains a pre-set initial sound velocity as the preliminary sound velocity, and wherein the preliminary sound velocity obtained in the first sound velocity obtaining step is employed as the second velocity when the determination result made in the image quality determining step is positive, and the first sound velocity calculated in the first sound velocity calculating step is employed as the second velocity when the determination result is negative.

19. A non-transitory computer readable recording medium having stored therein a program that causes a computer to execute signal processing for an ultrasound inspection apparatus for inspecting an inspection object using an ultrasonic beam, the program comprising:

a region setting step of setting a plurality of regions within the inspection object;

a first sound velocity calculating step of calculating a sound velocity of each of the plurality of regions as a first sound velocity;

a first sound velocity obtaining step of taking one of the plurality of regions as a first region of interest and further obtaining a preliminary sound velocity of the first region of interest, the preliminary sound velocity being different from the first sound velocity of the first region of interest and being obtained based on the first sound velocity of at least one of the plurality of regions temporally and/or spatially within the a predetermined distance from the first region of interest;

an image quality determining step of determining an image quality of the first region of interest based on the preliminary sound velocity obtained in the sound velocity obtaining step, a second sound velocity obtaining step of obtaining a second sound velocity of the first region of interest based on a determination result, and an image generating step of generating an ultrasound image based on the second sound velocity, wherein the first sound velocity obtaining step obtains a pre-set initial sound velocity as the preliminary sound velocity, and wherein the preliminary sound velocity obtained in the first sound velocity obtaining step is employed as the second velocity when the determination result made in the image quality determining step is positive, and the first sound velocity calculated in the first sound velocity calculating step is employed as the second velocity when the determination result is negative.

* * * * *